United States Patent
Shen et al.

(10) Patent No.: US 11,246,556 B2
(45) Date of Patent: Feb. 15, 2022

(54) SYSTEMS AND METHODS FOR MEDICAL IMAGE SCANNING POSITIONING

(71) Applicant: SHANGHAI UNITED IMAGING HEALTHCARE CO., LTD., Shanghai (CN)

(72) Inventors: Zhenhua Shen, Shanghai (CN); Qiang He, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 539 days.

(21) Appl. No.: 15/798,554

(22) Filed: Oct. 31, 2017

(65) Prior Publication Data
US 2018/0360409 A1 Dec. 20, 2018

(30) Foreign Application Priority Data
Jun. 16, 2017 (CN) .......................... 201710456295.7

(51) Int. Cl.
*A61B 6/00* (2006.01)
*A61G 11/00* (2006.01)
(Continued)

(52) U.S. Cl.
CPC ............ *A61B 6/547* (2013.01); *A61B 6/0487* (2020.08); *A61B 8/4263* (2013.01); *A61G 11/00* (2013.01);
(Continued)

(58) Field of Classification Search
CPC ....... A61B 6/547; A61B 6/0457; A61B 6/032; A61B 6/037; A61B 6/563; A61B 8/4263;
(Continued)

(56) References Cited

U.S. PATENT DOCUMENTS 4,026,654 A * 5/1977 Beaurain ................. G01S 17/50
356/5.07
4,334,495 A * 6/1982 Derkacs .................. B05B 12/12
118/313
(Continued)

FOREIGN PATENT DOCUMENTS

CN 1990062 A 7/2007
CN 101627917 A 1/2010
(Continued)

OTHER PUBLICATIONS

Li, Pengfei et al., Design of intelligent hospital bed based on single chip microcomputer, Fujian Computer, 124-125, 2017.
(Continued)

*Primary Examiner* — Amelie R Davis
*Assistant Examiner* — John Denny Ll
(74) *Attorney, Agent, or Firm* — Metis IP LLC

(57) ABSTRACT

Systems and methods for medical imaging diagnoses are provided. The methods may include detecting an entrance of the scan platform into a scanning room by a signal emission device, moving the scan platform to a joint area according to connection interface of the medical imaging device by a driving device. The method may also include adjusting the scan platform to connect to the medical imaging device by a position adjusting device. The method may also include connecting the scan platform to the medical imaging device
(Continued)

by a physical interface. The method may further include moving the scanning object to a scanning area of the medical imaging device by the driving device.

19 Claims, 14 Drawing Sheets

(51) Int. Cl.
| | |
|---|---|
| *A61B 8/00* | (2006.01) |
| *G05D 1/02* | (2020.01) |
| *A61B 6/04* | (2006.01) |
| *G01S 3/783* | (2006.01) |
| *G01B 11/14* | (2006.01) |
| *A61B 5/055* | (2006.01) |
| *A61B 6/03* | (2006.01) |
| *G05D 3/12* | (2006.01) |
| *G01V 8/20* | (2006.01) |

(52) U.S. Cl.
CPC .............. *G01B 11/14* (2013.01); *G01S 3/783* (2013.01); *G01V 8/20* (2013.01); *G05D 1/0225* (2013.01); *G05D 1/0234* (2013.01); *A61B 5/055* (2013.01); *A61B 6/032* (2013.01); *A61B 6/037* (2013.01); *A61B 6/563* (2013.01); *A61B 8/40* (2013.01); *A61B 8/54* (2013.01); *A61B 2503/04* (2013.01); *A61B 2562/12* (2013.01); *A61G 2203/22* (2013.01); *A61G 2210/50* (2013.01); *G05D 3/12* (2013.01); *G05D 2201/0206* (2013.01)

(58) Field of Classification Search
CPC .. A61B 8/40; A61B 8/54; A61B 5/055; A61B 2503/04; A61B 2562/12; A61G 11/00; A61G 2203/22; A61G 2210/50; G05D 1/0225; G05D 1/0234; G05D 3/12; G05D 2201/0206
See application file for complete search history.

(56) References Cited

U.S. PATENT DOCUMENTS

| | | | |
|---|---|---|---|
| 5,499,415 A | 3/1996 | McKenna | |
| 2008/0001735 A1* | 1/2008 | Tran | A61B 5/0488 340/539.22 |
| 2011/0067179 A1 | 3/2011 | Klemm et al. | |
| 2011/0116597 A1* | 5/2011 | Agrawal | G01N 23/04 378/57 |
| 2013/0129281 A1* | 5/2013 | Son | G02B 6/4245 385/33 |
| 2014/0094997 A1* | 4/2014 | Hyde | G05D 1/0246 701/2 |
| 2014/0331406 A1* | 11/2014 | Haider | A61G 7/08 5/600 |
| 2015/0177340 A1 | 6/2015 | Mori | |
| 2016/0081582 A1* | 3/2016 | Rapoport | G01R 33/30 600/415 |
| 2016/0089283 A1* | 3/2016 | DeLuca | A61G 1/0287 180/413 |
| 2016/0166216 A1* | 6/2016 | Igney | A61B 5/704 356/614 |
| 2017/0340498 A1* | 11/2017 | Tessmer | A61G 1/00 |
| 2018/0280223 A1* | 10/2018 | Hiratsuka | A61B 90/50 |
| 2018/0311822 A1* | 11/2018 | Kaminka | B25J 5/005 |
| 2019/0331810 A1 | 10/2019 | Yan et al. | |

FOREIGN PATENT DOCUMENTS

| | | |
|---|---|---|
| CN | 103142230 A | 6/2013 |
| CN | 204133609 U | 2/2015 |
| CN | 104665829 A | 6/2015 |
| EP | 0483729 | 5/1992 |

OTHER PUBLICATIONS

First Office Action in Chinese Application No. 201710456295.7 dated Feb. 27, 2020, 15 pages.

* cited by examiner

… (1) …

SYSTEMS AND METHODS FOR MEDICAL IMAGE SCANNING POSITIONING

CROSS-REFERENCE TO RELATED APPLICATIONS

This application claims priority of Chinese Patent Application No. 201710456295.7, filed on Jun. 16, 2017, which is expressly incorporated herein by reference in its entirety.

TECHNICAL FIELD

The present disclosure generally relates to medical imaging diagnoses, and more particularly to systems and methods for medical image scanning positioning.

BACKGROUND

In the course of treatment, a patient may need to conduct multiple medical imaging diagnoses such as the MRI (Magnetic Resonance Imaging) or CT (Computed Tomography). When conducting a medical imaging diagnosis, a patient may need to be transferred from a ward to a scanning room, where a medical imaging device is located. In the transferring process, the patient may be transferred from a sick bed to a transferring table for moving the patient to the scanning room. After moving to the scanning room, the patient may need be transferred again from the transferring table to a scan platform of the medical imaging device. In such complex transferring process, the patient needs to be transferred twice, which may take a long time. In addition, the movements of the body may cause the patient to suffer and even lead exacerbations of the illness. It may therefore be desirable to provide systems and methods to properly transfer the patient to the scanning room with low cost and less pain suffered by the patient.

SUMMARY

In an aspect of the present disclosure, a system is provided. The system may include a storage device storing a set of instructions. The system may also include one or more processors configured to communicate with the storage device. When executing the set of instructions, the one or more processors may cause the system to perform one or more of the following operations. The one or more processors may cause the system to detect, by a signal emission device, an entrance of a scan platform into a scanning room, the scan platform may be configured to support a scanning object. The one or more processors may also cause the system to move, by a driving device, the scan platform to a joint area according to the connection interface of the medical imaging device. The one or more processors may also cause the system to adjust, by a position adjusting device, the scan platform to connect to the medical imaging device. The one or more processors may also cause the system to connect, by a physical interface, the scan platform to the medical imaging device. The one or more processors may further cause the system to move, by the driving device, the scanning object to a scanning area of the medical imaging device.

In another aspect of the present disclosure, a method implemented on a computing device having one or more processors and a storage device is provided. The method may include one or more of the following operations. The method may include detecting, by a signal emission device, an entrance of a scan platform into a scanning room, the scan platform may be configured to support a scanning object. The method may also include moving, by a driving device, the scan platform to a joint area according to the connection interface of the medical imaging device. The method may also include adjusting, by a position adjusting device, the scan platform to connect to the medical imaging device. The method may also include connecting, by a physical interface, the scan platform to the medical imaging device. The method may further moving, by the driving device, the scanning object to a scanning area of the medical imaging device.

In yet another aspect of the present disclosure, a non-transitory computer readable medium is provided. The non-transitory computer readable medium storing instructions, the instructions, when executed by a computing device, may cause the computing device to effectuate a method. The method may include detecting, by a signal emission device, an entrance of a scan platform into a scanning room, the scan platform may be configured to support a scanning object. The method may also include moving, by a driving device, the scan platform to a joint area according to the connection interface of the medical imaging device. The method may also include adjusting, by a position adjusting device, the scan platform to connect to the medical imaging device. The method may also include connecting, by a physical interface, the scan platform to the medical imaging device. The method may further moving, by the driving device, the scanning object to a scanning area of the medical imaging device.

In some embodiments, the scan platform may be moved to the joint area. A position of the scan platform and a position of the joint area may be obtained. A route may be determined based on the position of the scan platform and the position of the joint area. The scan platform may be moved to the joint area according to the route.

In some embodiments, the scan platform may be connected to the medical imaging device. An optical signal transmitter may be actuated to emit optical signals toward two optical signal receivers, the optical signal transmitter being on one side of the joint area, the two optical signal receivers being configured to receive the optical signals emitted by the optical signal transmitter and being on another side of the joint area. An intensity of optical signals received by the two optical signal receivers may be determined. Whether the intensity of the optical signals received by the two optical signal receivers equals zero may be determined. The scan platform may be connected to the medical imaging device, in response to the determination that the intensity of the optical signals received by the two optical signal receivers equals zero.

In some embodiments, the position adjusting information of the scan platform may be determined based on the intensity of the optical signals received by the two optical signal receivers, in response to the determination that the intensity of the optical signals received by the two optical signal receivers does not equal zero. The position of the scan platform may be adjusted based on the position adjusting information.

In some embodiments, the scan platform may include a first optical fiber interface. The medical imaging device may include a second optical fiber interface. And the scan platform may be adjusted such that an orientation and a height of the first optical fiber interface match an orientation and a height of the second optical fiber interface, before the optical signal transmitter being actuated to emit optical signals to emit optical signals.

In some embodiments, a first detecting signal may be transmitted by the first optical fiber interface. A second detecting signal may be received by the second optical fiber interface. Whether the first detecting signal equals to the second detecting signal may be determined. A successful connection is established between the scan platform, and the medical imaging device may be determined, in response to the determination that the first detecting signal equals the second detecting signal. An indication indicative of the successful connection may be outputted.

In some embodiments, a successful connection is not established between the scan platform and the medical imaging device may be determined, in response to the determination that the first detecting signal does not equal the second detecting signal. The scan platform may be returned to connect to the medical imaging device.

In some embodiments, the scanning object may be moved to a scanning area of the medical imaging device. A set of moving parameters may be determined based on an initial position of the scanning object in the scan platform, a location of the scanning area and a position of scan platform after connecting with the medical imaging device. The scanning object may be moved to the scanning area based on the set of moving parameters.

In some embodiments, a first electrical signal instruction may be generated based on the set of moving parameters. The first electrical signal instruction may be converted into an optical signal instruction. The optical signal instruction may be transmitted from the second optical fiber interface to the first optical fiber interface. The optical signal instruction received by the first optical fiber interface may be converted into a second electrical signal instruction. The scanning object may be moved to the scanning area based on the second electrical signal instruction.

In some embodiments, the scan platform may be a pediatric scan platform including a bed body and an incubator.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
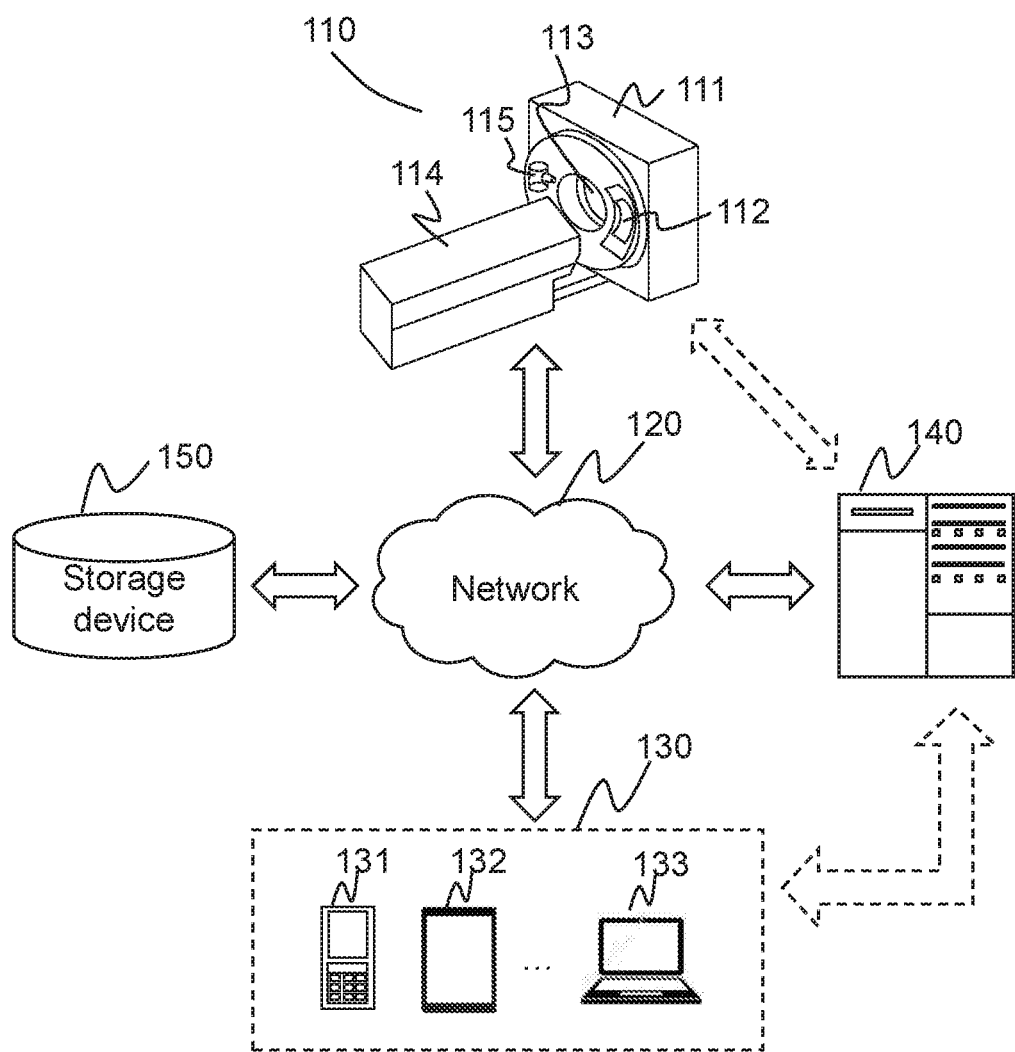
FIG. 1 is a schematic diagram illustrating an exemplary medical imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for illustration and description only and are not intended to limit the scope of the present disclosure. It is understood that the drawings are not to scale.

Provided herein are systems and components for medical imaging, such as for disease diagnosis or research purposes. In some embodiments, the imaging system may be a computed tomography (CT) system, a positron emission tomography (PET) system, an emission computed tomography (ECT) system, a magnetic resonance imaging (MRI) system, an ultrasonography system, an X-ray photography system, or the like, or any combination thereof.

For illustration purposes, the present disclosure is directed to systems and methods for medical imaging diagnoses. The system may transfer a patient to a scanning room for conducting the medical imaging diagnoses. The patient may be transferred by a scan platform. The scan platform may move to a joint area and connect to a medical imaging device. The patient lying on the scan platform may be moved to a scanning area in the medical imaging device to conduct a medical imaging diagnoses.

The following description is provided to help better understanding medical imaging methods and/or systems. Merely for illustration purposes, the term "scan platform" used in this disclosure may refer to a scanning bed, a sickbed, or a scan table corresponding to the medical imaging device. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

The present disclosure relates to systems and methods for medical imaging diagnoses. The systems may perform the methods to detect, by a signal emission device, an entrance of the scan platform into a scanning room. The system may also perform the methods to move, by a driving device, the scan platform to a joint area according to the connection interface of the medical imaging device. The systems may also perform the methods to adjust, by a position adjusting device, the scan platform to connect to the medical imaging device. The systems may also perform the methods to connect, by a physical interface, the scan platform to the medical imaging device. The systems may further perform the methods to move, by the driving device, the scanning object to a scanning area of the medical imaging device.

FIG. 1 is a schematic diagram illustrating an exemplary medical imaging system according to some embodiments of the present disclosure. In some embodiments, the medical imaging system 100 may be a single modality system. For example, the medical imaging system 100 may be a PET system, a CT system, an MRI system, or an ECT system. In some embodiments, the medical imaging system 100 may be a multimodality system. For example, the medical imaging system 100 may be a computed tomography-positron emission tomography (CT-PET) system, a magnetic resonance-positron emission tomography (MR-PET) system, or the like. As shown in FIG. 1, the medical imaging system 100 may include a medical imaging device 110, a network 120, one or more terminals 130, a processing device 140, and a storage device 150.

The medical imaging device 110 may include a gantry 111, a detector 112, a scanning area 113, a scan platform 114, and a radioactive scanning source 115. The gantry 111 may support the detector 112 and the radioactive scanning source 115. A scanning object may be placed on the scan platform 114 for scanning. The radioactive scanning source 115 may emit radioactive rays to the scanning object. The detector 112 may detect radiation events (e.g., gamma photons, X-ray) emitted from the scanning area 113. In some embodiments, the detector 112 may include one or more detector units. The detector units may include a scintillation detector (e.g., a cesium iodide detector), a gas detector, etc. The detector unit may be a single-row detector and/or a multi-rows detector.

The network 120 may include any suitable network that can facilitate the exchange of information and/or data for the medical imaging system 100. In some embodiments, one or more components of the medical imaging system 100 (e.g., the medical imaging device 110, the terminal 130, the processing device 140, the storage device 150) may communicate information and/or data with one or more other components of the medical imaging system 100 via the network 120. For example, the processing device 140 may obtain image data from the medical imaging device 110 via the network 120. As another example, the processing device 140 may obtain user instructions from the terminal 130 via the network 120. The network 120 may be a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network (VPN), a satellite network, a telephone network, routers, hubs, switches, server computers, or the like, or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical imaging system 100 may be connected to the network 120 to exchange data and/or information.

The terminal(s) 130 may include a mobile device 131, a tablet computer 132, a laptop computer 133, etc. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a HoloLens™, a Gear VR™, etc. In some embodiments, the terminal(s) 130 may be part of the processing device 140.

The processing device 140 may process data and/or information obtained from the medical imaging device 110, the terminal 130, and/or the storage device 150. For example, the processing device 140 may detect an entrance of a scan platform into a scanning room, move the scan platform 114 to a joint area to connect to the medical imaging device 110, and move a scanning object loaded on the scan platform to the scanning area 113 for a medical imaging diagnoses. In some embodiments, the processing device 140 may be a computer, a user console, a single server, a server group, etc. The server group may be centralized or distributed. In some embodiments, the processing device 140 may be local or remote. For example, the processing device 140 may access information and/or data stored in the medical imaging device 110, the terminal 130, and/or the storage device 150 via the network 120. As another example, the processing device 140 may be directly connected to the medical imaging device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components illustrated in FIG. 2.

The storage device 150 may store data, instructions, and/or any other information. In some embodiments, the storage device 150 may store data obtained from the medical imaging device 110, the terminal 130, and the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the medical imaging system 100 (e.g., the processing device 140, the terminal 130). One or more components of the medical imaging system 100 may access the data or instructions stored in the storage device 150 via the network 120. In some embodiments, the storage device 150 may be directly connected to or communicate with one or more other components of the medical imaging system 100 (e.g., the processing device 140, the terminal 130). In some embodiments, the storage device 150 may be part of the processing device 140.

Figure 2:
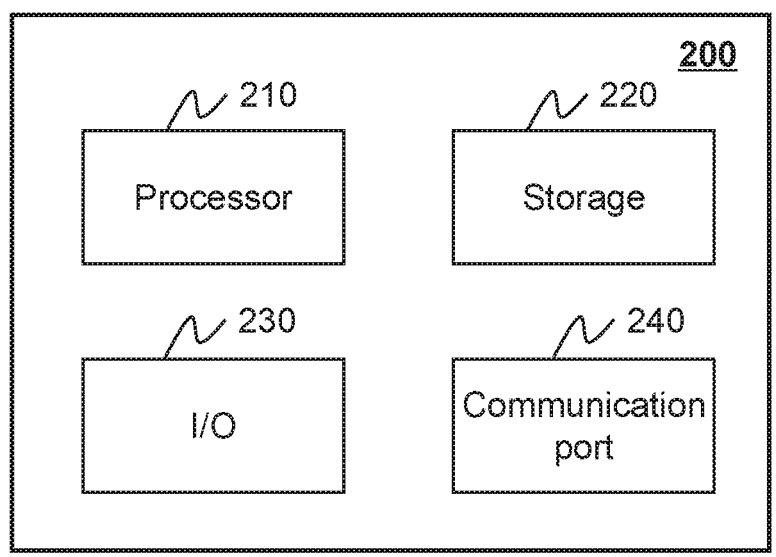
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform functions described herein. For example, the processor 210 may process image data obtained from the medical imaging device 110, the terminal 130, the storage device 150, and/or any other component of the medical imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the medical imaging device 110, the terminal 130, the storage device 150, and/or any other component of the medical imaging system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a regularization item.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 240 may be connected to a network (e.g., network 120) to facilitate data communications. The communication port 240 may establish connections between the processing device 140 and the medical imaging device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMAX™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
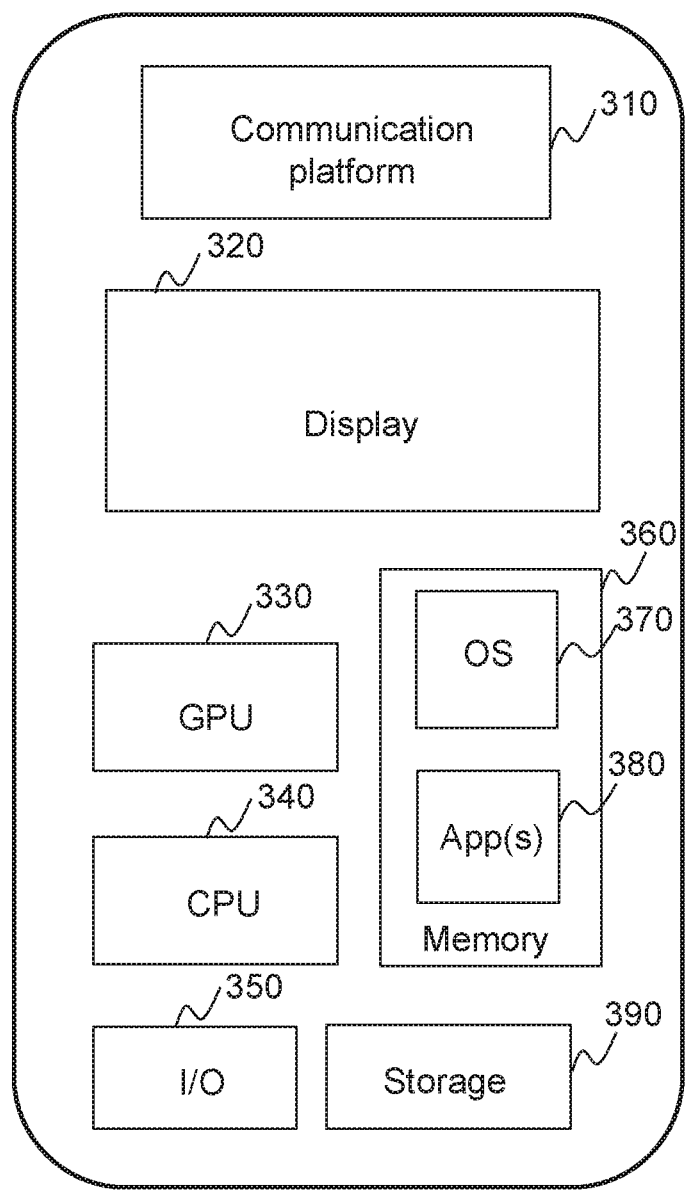
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system (OS) 370 (e.g., iOS™, Android™, Windows Phone™) and one or more applications 380 may be loaded into the memory 360 from the storage 390 to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
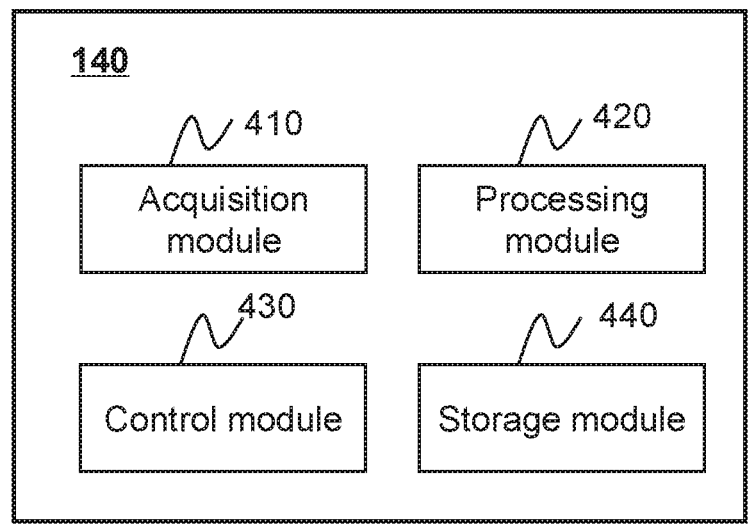
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an acquisition module 410, a processing module 420, a control module 430, and a storage module 440. Generally, the terms "module," "unit," and/or "engine" used herein, refers to logic embodied in hardware or firmware, or to a collection of software instructions. The modules, units, and engines described herein may be implemented as software and/or hardware modules and may be stored in any type of non-transitory computer-readable medium or another storage device. In some embodiments, a software module may be compiled and linked into an executable program. It will be appreciated that software modules can be callable from other modules or themselves, and/or can be invoked in response to detected events or interrupts. Software modules configured for execution on computing devices (e.g., the processor 210 of the computing device 200 and/or the CPU 340 of the mobile device 300s) can be provided on a computer readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules but can be represented in hardware or firmware. In general, the modules described herein refer to logical modules that can be combined with other modules or divided into sub-modules despite their physical organization or storage.

The acquisition module 410 may acquire data from other components of the medical imaging system 100. For example, the acquisition module 410 may acquire data related to the wireless signals transmitted by a signal emission device (e.g. a wireless signal transmitter) arranged on the scan platform 114. The data may include the intensity information of the wireless signals. According to data related to the intensity information, the processing device 140 may determine whether the scan platform 114 has entered the scanning room.

In some embodiments, the acquisition module 410 may acquire data stored in the storage module 440. After the scan platform entering the scanning room, the processing device 140 may control the scan platform to move into a joint area according to a route. For example, the route may be a historical record of the movement route from the entrance of the scanning room to the joint area stored in the storage module 440. As another example, when the scan platform 114 enters the scanning room for the first time, the acquisition module 410 may acquire position information of the medical imaging device 110 and position information of the scan platform 114 in the scanning room. The position information of the medical imaging device 110 may be obtained from a design drawing, a photo from a camera arranged in the scanning room, a positioning device, or the like. The position information of the scan platform 114 may be determined by a positioning device. The position information of the medical imaging device 110 and the position information of the scan platform 114 may be stored in the storage module 440.

In some embodiments, the acquisition module 410 may acquire data related to optical signals. For example, after the scan platform 114 moves into the joint area, one or more optical signal transmitters arranged on the scan platform 114 may be actuated to emit optical signals. The optical signal may be received by at least two optical signal receivers arranged in the scanning room. According to the data related to the optical signals, the processing device 140 may determine whether the scan platform 114 has been moved to an appropriate position in the joint area.

In some embodiments, the acquisition module 410 may acquire data from optical fiber interfaces arranged on the scan platform 114 and the medical imaging device 110. For example, after the scan platform 114 moves to the appropriate position, the optical fiber interface may be actuated to transmit optical signals. The optical fiber interface arranged on the medical imaging device 110 may receive the optical signals. The data acquired by the acquisition module 410 may be related to the intensity and/or amount of the optical signals. According to the data acquired by the acquisition module 410, the processing device 140 may determine a connection between the scan platform 114 and the medical imaging device 110 has been successfully established.

The processing module 420 may process the information provided by various components or modules of medical imaging system 100. The processing module 420 may process the data acquired by acquisition module 410, the data retrieved from the storage module 440, etc. In some embodiments, according to the data acquired by acquisition module 410, the processing module 420 may generate various operation instructions. For example, when acquiring the data relating to the entrance of the scan platform 114 into the scanning room, the processing module 420 may generate an entering completing instruction, which may lead the acquisition module 410 to acquire the route from the storage module 440. As another example, after the scan platform 114 moves into the joint area according to the route, the processing module 420 may generate a movement completing instruction, which may lead the scan platform to perform the connection process. As still another example, after the scan platform 114 connects to the medical imaging device 110, the processing module 420 may generate a connection completing instruction, which may lead the scan platform 114 to perform a movement of an incubator to the scanning area. As yet another example, after a scanning object is moved to the scanning area, the processing module 420 may generate a scanning object moving completing instruction, which may lead the medical imaging device 110 to perform a scanning process. In some embodiments, the instructions generated by the processing module 420 may transmit to any other modules of processing device 140 for performing corresponding operations.

The control module 430 may control operations of one or more components or modules of the medical imaging system 100.

In some embodiments, the control module 430 may control operations of scan platform 114. For example, when received the entering completing instruction, the control module 430 may control the scan platform 114 to move to the joint area according to the route acquired from the storage module 440. As another example, when received the movement completing instruction, the control module 430 may control the scan platform 114 to connect to the medical imaging device. As still another example, when received the connection completing instruction, the control module 430 may control the scanning object on the scan platform 114 to move to the scanning area in the medical imaging device 110. As yet another example, when receiving the scanning object moving completing instruction, the control module 430 may control the medical imaging device 110 to perform the scanning process.

In some embodiments, the control module 430 may control operations of the acquisition module 410, the storage module 440, and/or the processing module 420 (e.g., by generating one or more control parameters). For example, the control module 430 may control the processing module 420 to process the scan data acquired by the acquisition module 410.

In some embodiments, the control module 430 may receive a real-time command or retrieve a predetermined command provided by a user (e.g., a doctor) to control one or more operations of the acquisition module 410 and/or the processing module 420. For example, the control module 430 may adjust the acquisition module 410 and/or the processing module 420 to obtain images of a scanning subject according to the real-time command and/or the predetermined command. In some embodiments, the control module 430 may communicate with one or more other modules of the processing device 140 for exchanging information and/or data.

The storage module 440 may store control parameters, control instructions, scan data, processed scan data, scout image, reconstruction images, or the like, or any combination thereof. In some embodiments, the storage 440 may store one or more programs and/or instructions that may be executed by the processing module 420 of processing device 140 to perform exemplary processes or methods described in this disclosure. For example, the storage 440 may store program(s) and/or instruction(s) that can be executed by the processing module 420 of the processing device 140 to acquire scan data, reconstruct an image based on the scan data, and/or display any intermediate result or a resultant image.

In some embodiments, one or more modules illustrated in FIG. 4 may be implemented in at least part of the exemplary medical imaging system illustrated in FIG. 1. For example, the acquisition module 410, the control module 430, the storage module 440, and/or the processing module 420 may be integrated into a console (not shown). Via the console, a user may set parameters for scanning an object, controlling imaging processes, controlling parameters for reconstruction of an image, viewing reconstructed images, etc. In some embodiments, the console may be implemented via the processing device 140 and/or the terminal 130.

Figure 5:
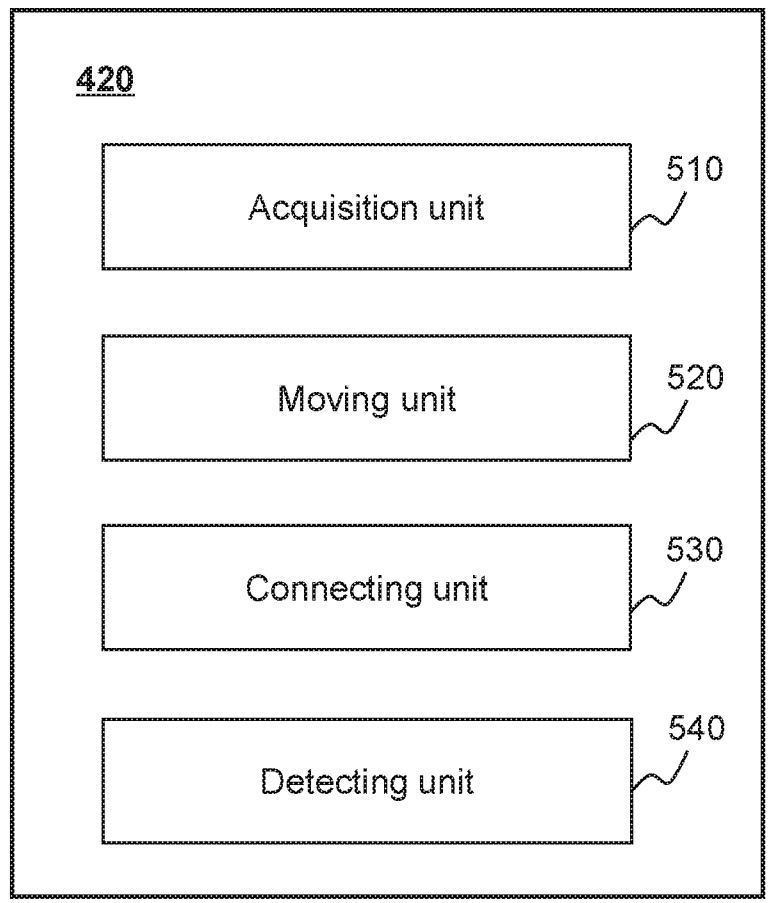
FIG. 5 is a block diagram illustrating an exemplary processing module according to some embodiments of the present disclosure.

FIG. 5 is a block diagram illustrating an exemplary processing module 420 according to some embodiments of the present disclosure. The processing module 420 may include an acquisition unit 510, a moving unit 520, a connecting unit 530, and a detecting unit 540. The processing module 420 may be implemented on various components (e.g., the processor 210 of the computing device 200 illustrated in FIG. 2).

The acquisition unit 510 may acquire wireless signal transmitted by the scan platform 114. The intensity of the wireless signal may be related to the distance of the scan platform 114. Therefore, the processing device 140 may determine whether the scan platform 114 has entered the scanning room according to the intensity of the wireless signal acquired by the acquisition unit 510. The acquisition unit 510 may also acquire historical route from the storage module 440. The historical route may be the historical record of the movement route of the scan platform 114 from the entry of the scanning room to the joint area.

The moving unit 520 may determine a route for the scan platform 114 to move to the joint area. If a historical route exists, the moving unit 520 may determine the historical route as the route. When the scan platform 114 enter the scanning room for the first time, and no historical routes are stored in the storage module 440, the moving unit 520 may determine the route according to the position information of the medical imaging device 110 and the position information of the scan platform 114 acquired by the acquisition unit 510.

In some embodiments, the moving unit 520 may determine a set of moving parameters for the scanning object to move into the scanning area. For example, after the scan platform 114 connects to the medical imaging device 110, a camera arranged in the medical imaging device 110 may take an image of the scanning object. Moreover, the moving unit 520 may determine the set of moving parameters based on the image of the scanning object.

The connecting unit 530 may determine a connection of the scan platform 114 to the medical imaging device 110. For example, after the scan platform 114 moves to the joint area, at least one optical signal transmitters arranged on the scan platform 114 may be actuated to transmit optical signals and at least two optical signal receivers arranged in the scanning room may receive the optical signals. The at least one optical signal transmitters and the at least two optical signal receivers may be arranged in two opposite sides of the joint area. Also, the at least one optical signal transmitters and the at least two optical signal receivers may be arranged according to the detail position information of the medical imaging device in the scanning room.

The detecting unit 540 may determine an orientation and a height of the scan platform 114 for connecting to the medical imaging device 110. For example, after the scan platform 114 moves to the scanning area, the processing device 140 may adjust the orientation and height of the scan platform 114. A first optical fiber interface may be arranged on the scan platform 114 and a second optical fiber interface may be arranged on the medical imaging device 110. The first optical fiber interface may transmit optical signals and the second optical fiber interface may receive the optical signals. The detecting unit 540 may determine orientation and height of the scan platform according to the amount and intensity of the optical signals transmitted by the first optical fiber interface and received by the second optical fiber interface.

It should be noted that the above description of the processing module 420 is merely provided for illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more units in the processing module 420 may include an independent storage block (not shown) respectively. As another example, any two or more units may be combined as an independent unit used to implement more than one functions. As still another example, any one of the units may be divided into two or more sub-units.

Figure 6:
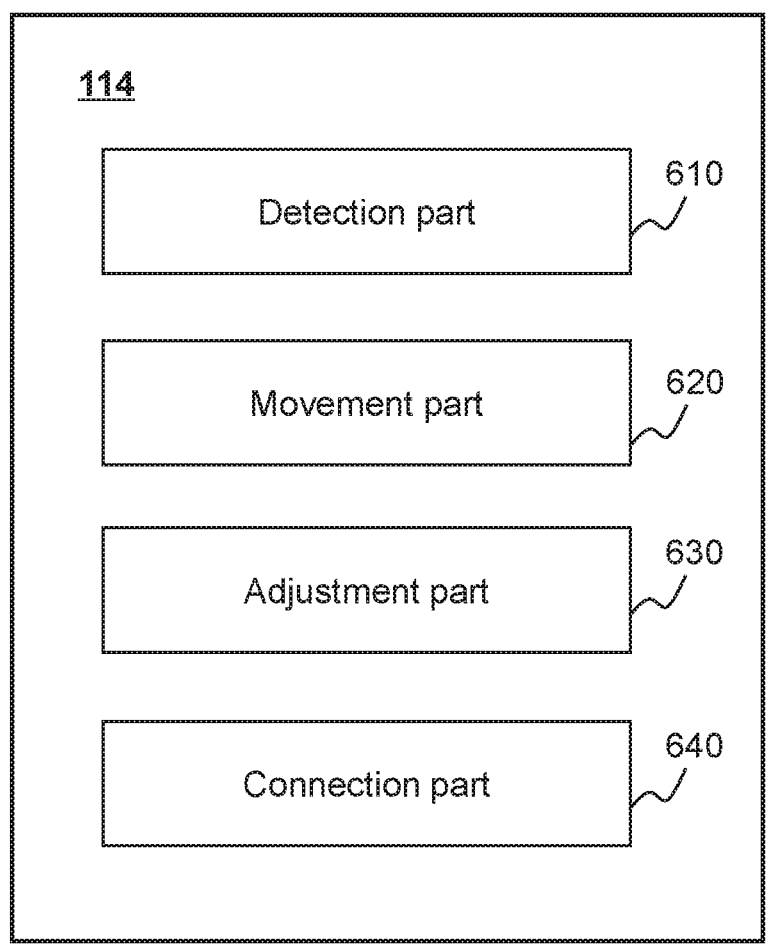
FIG. 6 is a block diagram illustrating hardware components of an exemplary scan platform according to some embodiments of the present disclosure.

FIG. 6 is a block diagram illustrating hardware components of an exemplary scan platform 114 according to some embodiments of the present disclosure. The scan platform 114 may include a detection part 610, a movement part 620, an adjustment part 630, and a connection part 640.

The detection part 610 may be a positioning device (not shown) arranged on the scan platform 114. The positioning device may be configured to determine whether the scan platform 114 has entered the scanning room. For example, the positioning device may include a signal emission device and/or a signal receiving device. In some embodiments, the signal emission device may be a wireless signal transmitter. In some embodiments, the signal receiving device may be a wireless signal receiver. The processing device 140 may determine whether the scan platform 114 has entered the scanning room according to the intensity of the wireless signals transmitted by the wireless signal transmitter and/or the wireless signals received by the wireless signal receiver.

The movement part 620 may be a driving device (not shown) configured to move the scan platform 114. In some embodiments, the driving device may be configured to drive the scan platform 114 to the scanning area. For example, the driving device may receive a moving instruction sent by the processing device 140. The moving instruction may include a route for the scan platform 114 determined by the processing device 140. The driving device may control the scan platform 114 to move into the joint area according to the route. In some embodiments, the driving device may also be configured to move the scanning object on the scan platform 114 to the scanning area. For example, after the scan platform 114 connects to the medical imaging device 110, the processing device 140 may determine a set of moving parameters. According to the set of moving parameters, the driving device may control the scanning object to move to the scanning area. In some embodiments, the driving device configured to drive the scan platform 114 to the scanning area may be different from the driving device configured to move the scanning object on the scan platform 114 to the scanning area. In some embodiments, a driving device may have two stages to drive the scan platform 114 to the scanning area and move of the scanning object the scanning area under different circumstances. For example, when receiving the moving instruction from the processing device 140, the driving device may select stage 1 to drive the scan platform 114 to the scanning area. After the scan platform 114 connecting to the medical imaging device 110, the driving device may shift to stage 2 to move the scanning object on to the scanning area.

The adjustment part 630 may include the optical signal transmitters configured to transmit optical signals. In some embodiments, there may be optical signal receivers configured to receive the optical signals. The optical signal receivers may be arranged in the scanning room. The optical signal transmitters and the optical signal receivers may be configured to adjust the position of the scan platform 114 in the joint area. For example, the optical signal transmitters may be arranged on one side of the joint area, and the optical signal receivers may be arranged on the other side of the joint area. The optical signal transmitters may be configured to transmit optical signals toward the optical signal receivers, and the optical signal receivers may be configured to receive the optical signals. In some embodiments, a transparent region may be arranged on the scan platform 114. The optical signals emitted by the optical signal transmitters may pass through the transparent region toward the optical signal receivers. The height of the center of the transparent region may be equal to the height of the optical signal transmitters and the optical signal receivers. Two shading components (e.g., two shading boards, two shading blocks) are arranged in the transparent region for blocking the optical signals. If the two shading components located between the optical signal transmitters and the optical signal receivers, the optical signals may be blocked or weakened, the intensity of the optical signals received by the optical signal receivers may be equal or close to zero. The processing device 140 may adjust a moving path of the scan platform 114 and control the scan platform 114 to move to an appropriate position according to the adjusting moving path. When the scan platform 114 is moved to the appropriate position, the intensity of the optical signals received by the optical signal receivers may equal zero.

Alternatively, a shading region may be arranged on the scan platform 114. The optical signals may be blocked by the shading region. The height of a center of the shading region may equal to the optical signal transmitters and the optical signal receivers. Two transparent subregions are arranged in the shading region for the optical signals to pass through. If the two transparent subregions located between the optical signal transmitters and the optical signal receivers, the optical signals may pass through, which means the intensity of the optical signals received by the optical signal receivers may be larger than zero. The processing device 140 may adjust a moving path of the scan platform 114 and control the scan platform 114 to move to an appropriate position according to the adjusting moving path. When the scan platform 114 is moved to the appropriate position, the intensity of the optical signals received by the optical signal receivers may be larger than zero.

The connection part 640 may be a physical interface. In some embodiments, the physical interface may be a first optical fiber interface arranged on the scan platform 114. The first optical fiber interface may be configured to adjust the orientation and height of the scan platform 114. For example, after the scan platform 114 moves to the joint area, the first optical fiber interface arranged on the scan platform 114 may be actuated to emit optical signals. The optical signals may be received by the second optical fiber interface arranged on the medical imaging device 110. By comparing the amount and intensity of the optical signals transmitted by the first optical fiber interface and received by the second optical fiber interface, the processing device 140 may determine whether the scan platform 114 is in the same orientation and height of the medical imaging device 110.

It should be noted that the above description of the hardware components of scan platform 114 is merely provided for illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more hardware parts of scan platform 114 may include an independent component (not shown) respectively. As another example, any two or more parts may be combined as an independent part used to implement more than one functions. As a further example, any one of the parts may be divided into two or more sub-parts.

Figure 7:
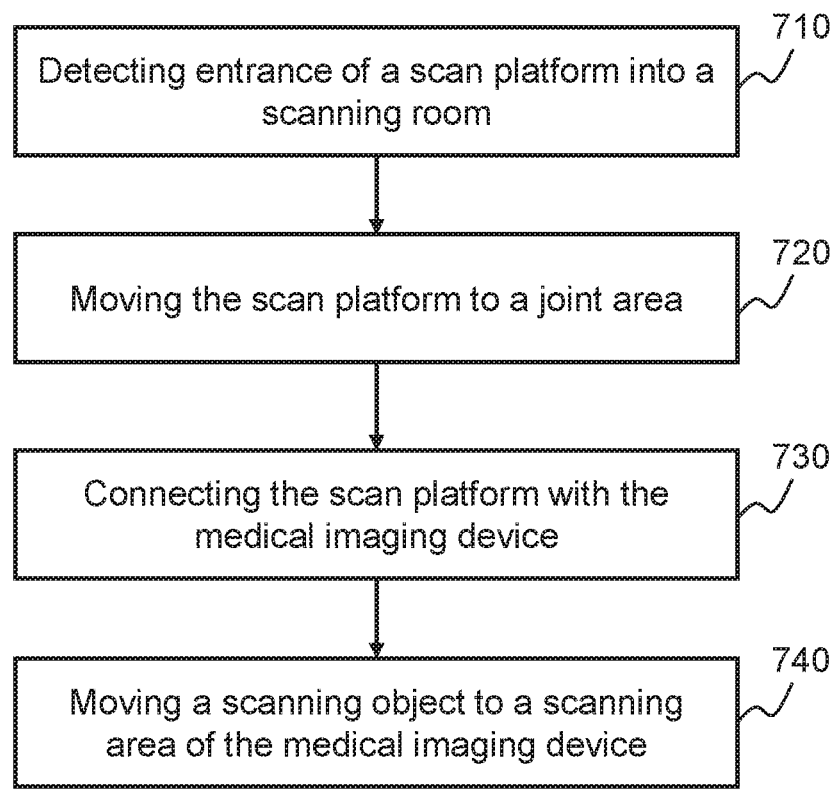
FIG. 7 is a flowchart illustrating an exemplary process for moving a scanning object to a scanning area according to some embodiments of the present disclosure.

FIG. 7 is a flowchart illustrating an exemplary process for moving a scanning object to a scanning area according to some embodiments of the present disclosure. In some embodiments, one or more operations of the process 700 illustrated in FIG. 7 for moving the scanning object to the scanning area may be implemented in the medical imaging system 100 illustrated in FIG. 1. For example, the process 700 illustrated in FIG. 7 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3).

In 710, the processing device 140 (e.g., the processing module 420, the acquisition unit 510 of the processing module 420, the detecting unit 540 of the processing module 420) may detect an entrance of the scan platform 114 into the scanning room. The scan platform 114 may be configured to support the scanning object (e.g., the scanning object described in FIG. 13*a*). In some embodiments, a wireless signal transmitter may be arranged on the scan platform 114. The wireless signal transmitter may transmit a wireless signal. The intensity of the wireless signal may relate to the distance of the scan platform 114. The processing device 140 may receive the wireless signal and determine the strength of the received wireless signal. The processing device 140 may also determine whether the scan platform 114 has entered the scanning room according to the strength of the acquired wireless signal.

In 720, the processing device 140 (e.g., the processing module 420, the control module 430, the moving unit 520 of the processing module 420) may control the scan platform 114 to move into a joint area. In some embodiments, after detecting the entrance of the scan platform 114 into the scanning room, the processing device 140 may control the scan platform 114 to move into a joint area. The joint area may be determined by the optical signal transmitters and the optical signal receivers arranged in the scanning room. A route may be determined by the processing device 140 for the scan platform 114. The route may be stored in the storage module 440. The route may be a historical record of the movement. If none historical record of the movement route is stored in the storage module 440, the processing device 140 may determine the route for the scan platform 114 according to the position information of the scan platform 114, the internal image information of the scanning room and the position information of the joint area. The position information of the scan platform 114 may be obtained by a wireless position technology (e.g., ZigBee technology described in the FIG. 13*b*). The internal image information of the scanning room may be obtained from one or more cameras arranged in the scanning room. The position information of the joint area may be determined based on the optical signal transmitters and the optical signal receivers arranged in the scanning room.

In 730, the processing device 140 (e.g., the processing module 420, the control module 430, the connecting unit 530 of the processing module 420) may control the scan platform 114 to connect to the medical imaging device 110. In some embodiments, after the scan platform 114 moves to the joint area, one or more optical signal transmitters arranged on the scan platform 114 may transmit optical signals, and at least two optical signal receivers arranged on the wall of the scanning room may receive the optical signals. The optical signal transmitters and the optical signal receivers may be arranged in two opposite sides of the joint area. The optical signal transmitters and the optical signal receivers may also be arranged according to detail position information of the medical imaging device 110 in the scanning room.

As an example, a transparent region may be arranged on the scan platform 114, and two shading components (e.g., two shading boards, two shading blocks) are arranged in the transparent region. The processing device 140 may determine an appropriate position for the scan platform 114 in the joint area based on the two shading components. As another example, a shading region may be arranged on the scan platform 114, and two transparent subregions may be arranged in the shading region. The processing device 140 may determine an appropriate position for the scan platform 114 in the joint area based on the two transparent subregions. The processing device 140 may control the scan platform 114 to move to the appropriate position and cause the scan platform 114 to connect to the medical imaging device 110.

In 740, the processing device 140 (e.g., the processing module 420, the control module 430, the moving unit 520 of the processing module 420) may cause a scanning object to move to a scanning area of the medical imaging device 110. In some embodiments, after connecting the scan platform 114 to the medical imaging device 110, the processing device 140 may determine a set of moving parameters for the scanning object to be moved into the scanning area. The set of moving parameters may be determined according to a scout image. The scout image may be a photo taken by a camera (not shown) arranged in the medical imaging device 110, and the processing device 140 may determine the moving parameters according to the photo.

It should be noted that the above description is provided for illustration, not intended to limit the scope of the present disclosure. For persons having ordinary skills in the art, multiple variations and modifications may be reduced to practice in the light of the present disclosure. For example, the process 700 may further include an operation for detecting whether the scan platform 114 has successfully connected to the medical imaging device 110. However, those variations and modifications do not depart from the scope of the present disclosure.

Figure 8:
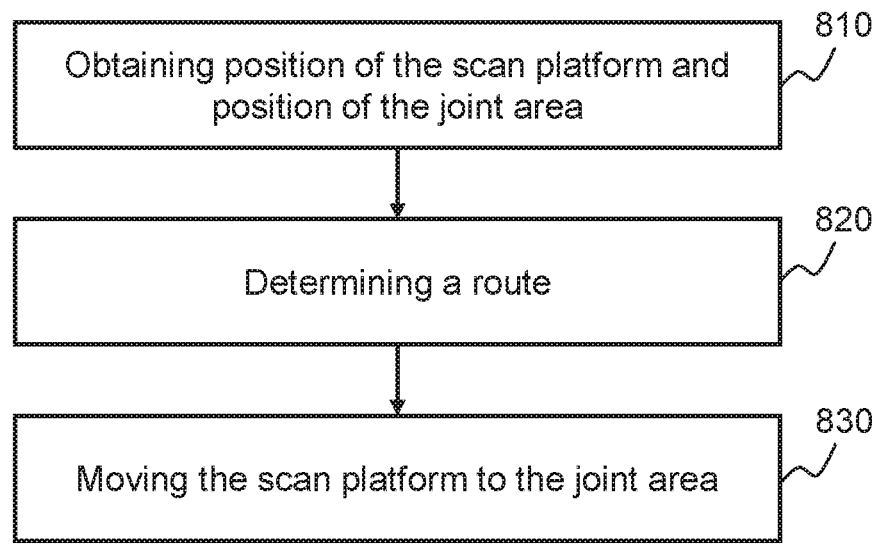
FIG. 8 is a flowchart illustrating an exemplary process for moving a scan platform to a joint area according to some embodiments of the present disclosure.

FIG. 8 is a flowchart illustrating an exemplary process for moving a scan platform 114 to the joint area according to some embodiments of the present disclosure. In some embodiments, one or more operations of the process 800 illustrated in FIG. 8 for moving the scan platform 114 to the joint area may be implemented in the medical imaging system 100 illustrated in FIG. 1. For example, the process 800 illustrated in FIG. 8 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3). In some embodiments, operation 720 of the process 700 may be performed according to the process 800.

In 810, the processing device 140 (e.g., the processing module 420, the acquisition unit 510 of the processing module 420, the detecting unit 540 of the processing module 420) may obtain the position of the scan platform 114 and the position of the joint area. In some embodiments, the position of the scan platform 114 may be determined by the processing device 140 according to a wireless position technology (e.g., ZigBee technology). The position of the joint area in the scanning room may be determined by the optical signal transmitters and the optical signal receivers arranged in the scanning room as described elsewhere in this disclosure.

In 820, the processing device 140 (e.g., the processing module 420) may determine a route for the scan platform 114 to move into the joint area. In some embodiments, when the scan platform 114 enters the scanning room for the first time, the processing device 140 may determine the route based on the position of the scan platform 114 and the position of the joint area. In some embodiments, if one or more obstacles exist in the scanning room, the processing device 140 may consider the positions of the obstacles for determining the route. The processing device 140 may obtain the positions of the obstacles by analyzing the photo of the interior of the scanning room taken by one or more cameras (not shown). It should be noted that the obstacles may include a doctor who may be moving in real time, so the route may also be adjusted by the processing device 140 in real time to avoid coming in contact with the doctor.

In 830, the processing device 140 (e.g., the processing module 420, the control module 430, the moving unit 520)

may control the scan platform 114 to move into the joint area. After the route determined by the processing device 140, the scan platform 114 may be moved to the joint area according to the route.

It should be noted that the above description is provided for illustration, not intended to limit the scope of the present disclosure. For persons having ordinary skills in the art, multiple variations and modifications may be reduced to practice in the light of the present disclosure. For example, the process 800 may further include an operation for obtaining the internal image information of the scanning room. For another example, operation 810 may be optional, and the route may be directly obtained from the storage module 440. However, those variations and modifications do not depart from the scope of the present disclosure.

Figure 9:
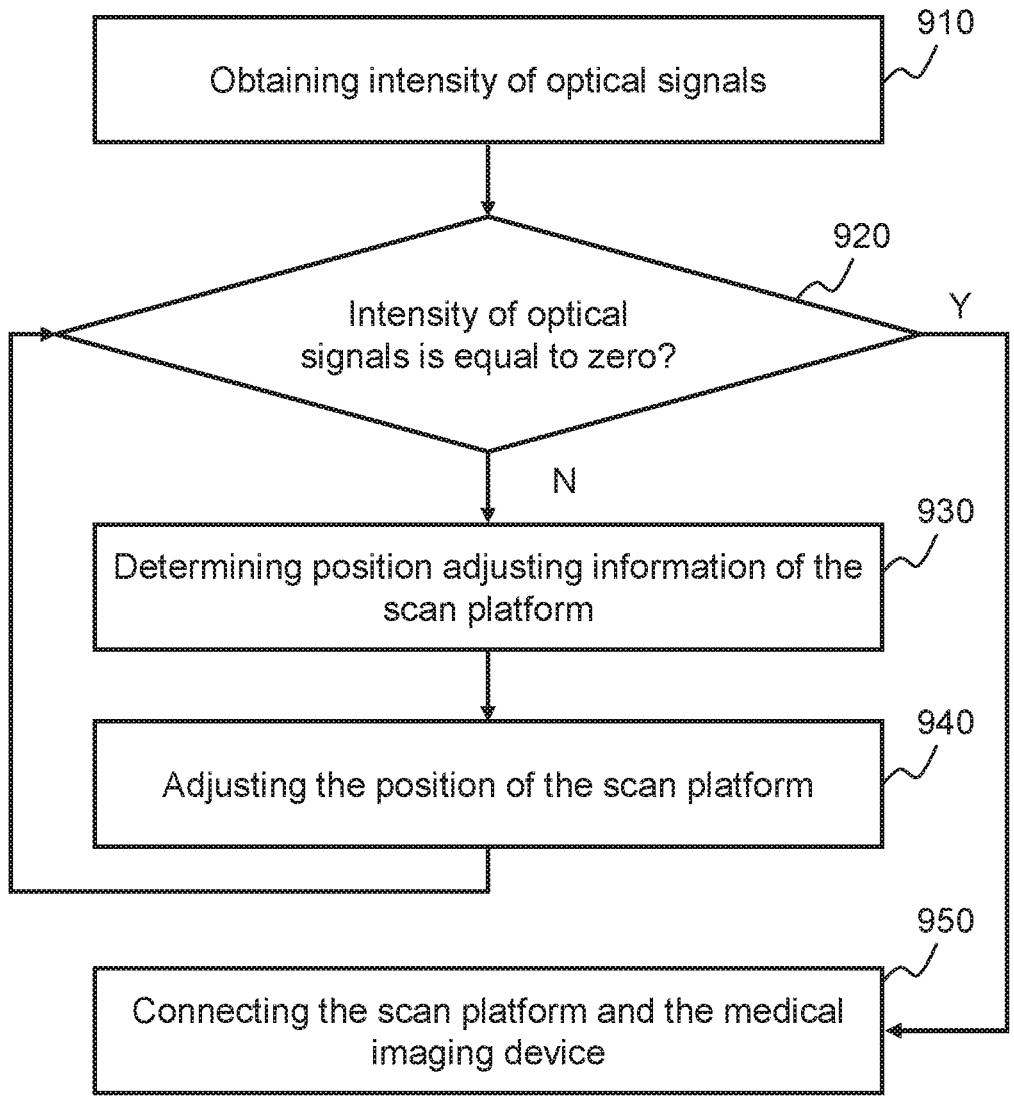
FIG. 9 is a flowchart illustrating an exemplary process for connecting a scan platform to a medical imaging device according to some embodiments of the present disclosure.

FIG. 9 is a flowchart illustrating an exemplary process for connecting a scan platform 114 to the medical imaging device 110 according to some embodiments of the present disclosure. In some embodiments, one or more operations of the process 900 illustrated in FIG. 9 for connecting the scan platform 114 to the medical imaging device 110 may be implemented in the medical imaging system 100 illustrated in FIG. 1. For example, the process 900 illustrated in FIG. 9 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3). In some embodiments, the operation 730 of the process 700 may be performed according to the process 900.

In 910, the processing device 140 (e.g., the processing module 420, the acquisition unit 510 of the processing module 420, the detecting unit 540 of the processing module 420) may obtain the intensity of the optical signals. In some embodiments, the optical signals may be transmitted by the one or more optical signal transmitters arranged in the scanning room. The optical signals may be received by at least two optical signal receivers. The optical signal transmitters and the optical signal receivers may be oppositely arranged on the sides of the joint area. The heights of the optical signal transmitters and the optical signal receivers may be the same. The positions of the optical signal transmitters and the optical signal receivers may be determined according to the position of the medical imaging device 110 in the scanning room. The optical signal transmitters may be fiber transmitters with a certain divergence angle. The optical signal receivers may be optical sensors. The processing device 140 may obtain intensity information of the optical signals received by the optical sensors (not shown) arranged in the scanning room.

In 920, the processing device 140 (e.g., the processing module 420) may determine whether the intensity of the optical signals received by the optical signal receivers is equal to zero. In some embodiments, a transparent region may be arranged on the scan platform 114 and two shading components (e.g., two shading boards, two shading blocks) are arranged in the transparent region. After the scan platform 114 moves to the joint area, the optical signals transmitted by the optical signals transmitters may pass through the transparent region of the scan platform 114 and be received by the optical signal receivers. When the optical signals are blocked by the two shading components, the optical signal receivers may not receive the optical signals. The processing device 140 may determine the intensity of the optical signals received by the optical signal receivers to be zero. Only when the optical signals are both blocked by the two shading components, the processing device 140 may determine the intensity of the both optical signals to be zero, and the process 900 may proceed to 950. When only one of the optical signals are blocked by one of the two shading components, the processing device 140 may determine the intensity of the corresponding optical signal to be zero, and the process 900 may proceed to 930. It should be noted that a situation of a shading region including two transparent subregions may also be permitted. The optical signal may pass through the two transparent subregions, and the corresponding optical signal receiver may receive the optical signal. When both optical signals pass through the two shading components, the processing device 140 may determine the intensity of the two optical signals is larger than zero and proceed to operation 950.

In 930, the processing device 140 (e.g., the processing module 420) may determine position adjusting information of the scan platform 114. The position adjusting information may be an adjustment to the moving path of the scan platform 114. For example, the two shading components may include a left shading component and a right shading component. When the optical signal is only blocked by the left shading component, the processing device 140 may determine the position adjusting information to be the adjustment to the moving path of the scan platform 114 to move to the right. When the optical signal is only blocked by the right shading component, the processing device 140 may determine the position adjusting information to be the adjustment to the moving path of the scan platform 114 to move to the left. It should be noted that an adjusting time threshold may be set by the processing device 140. When the actual adjusting times are larger than the adjusting time threshold, the processing device 140 may determine the position adjusting information to be the adjustment to the moving path of the scan platform 114 to move toward the optical signal transmitter.

In 940, the processing device 140 (e.g., the processing module 420, the control module 430, the moving unit 520) may adjust the position of the scan platform 114. In some embodiments, after the processing device, 140 determines the position adjusting information, the scan platform 114 may be controlled to move according to the position adjusting information by a position adjusting device. After adjusting the position of the scan platform 114, the processing device 140 may return to execute the operation 920 to determine whether the intensity of the optical signals is equal to zero based on the adjusted position of the scan platform 114.

In 950, the processing device 140 (e.g., the processing module 420, the connecting unit 530) may connect the scan platform 114 to the medical imaging device 110. In some embodiments, after the position of the scan platform 114 is adjusted, the optical signals may be blocked by the two shading components. Both two optical signal receivers may not receive optical signals. The intensity of the optical signals may be determined by the processing device 140 to be zero. The adjusted position of the scan platform 114 may be an appropriate position for the scan platform 114. The processing device 140 may connect the scan platform 114 to the medical imaging device 110 after the scan platform 114 moves to the appropriate position.

It should be noted that the above description is provided for illustration, not intended to limit the scope of the present disclosure. For persons having ordinary skills in the art, multiple variations and modifications may be reduced to practice in the light of the present disclosure. For example, the process 900 may further include an operation for obtaining an adjusting time threshold to limit the adjusting progress. For another example, operation 910 may be changed to obtain the position information of the optical signals irradiating on the scan platform 114, and the processing device 140 may further adjust the position of the scan platform 114 based on the position information of the optical signals irradiating on the scan platform 114. However, those variations and modifications do not depart from the scope of the present disclosure.

Figure 10:
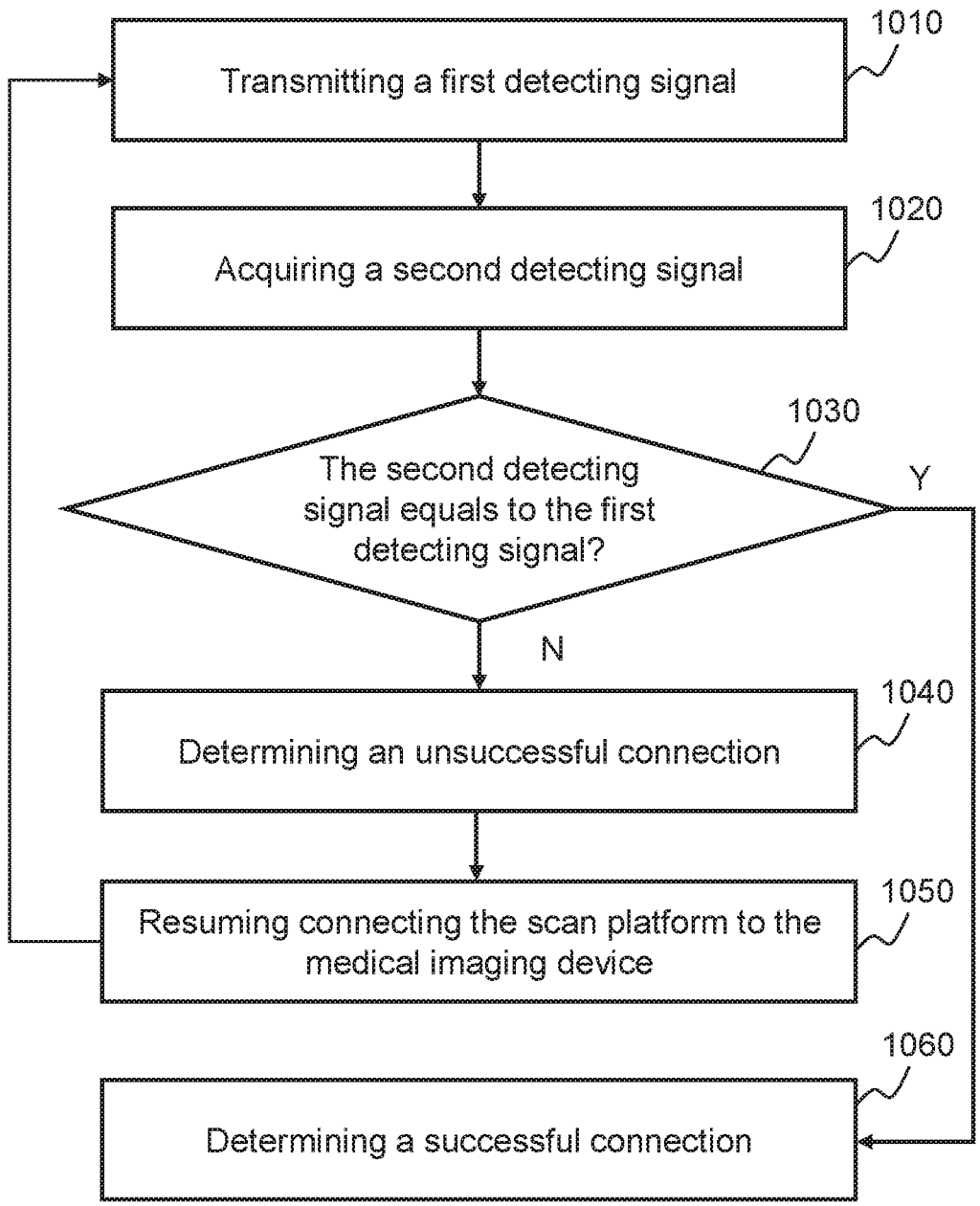
FIG. 10 is a flowchart illustrating an exemplary process for connecting a scan platform to a medical imaging device according to some embodiments of the present disclosure.

FIG. 10 is a flowchart illustrating an exemplary process for connecting a scan platform 114 to a medical imaging device 110 according to some embodiments of the present disclosure. In some embodiments, one or more operations of the process 1000 illustrated in FIG. 10 for medical image scanning positioning may be implemented in the medical imaging system 100 illustrated in FIG. 1. For example, the process 1000 illustrated in FIG. 10 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3). In some embodiments, the operation 950 of the process 900 may be performed according to the process 1000.

In 1010, the processing device 140 (e.g., the processing module 420, the control module 430) may cause, for example, a first optical fiber interface on the scan platform 114, to transmit a first detecting signal. In some embodiments, the amount and/or the intensity of the first detecting signal may be set based on a user input, or a default setting of the medical imaging system 100. Merely by way of example, the amount of the first detecting signal may be one beam, two beams, three beams, etc. In some embodiments, the amount and/or the intensity of the first detecting signal may be random. The first optical fiber interface may be a physical interface configured to connect an optical fiber cable. The optical fiber cable may be configured to convey the first detecting signal. In some embodiments, there may be an optical fiber connector between the first optical fiber interface and the optical fiber cable.

In 1020, the processing device 140 (e.g., the processing module 420, the control module 430) may cause, for example, a second optical fiber interface on the medical imaging device 110, to acquire a second detecting signal. Detail of the second optical fiber interface may be same with the first optical fiber interface illustrated in operation 1010.

In 1030, the processing device 140 (e.g., the processing module 420) may determine whether the first detecting signal equals to the second detecting signal. In some embodiments, to determine whether the first detecting signal equals to the second detecting signal, the processing device 140 may compare the amount and/or the intensity of the first detecting signal with that of the second detecting signal. For example, the processing device 140 may determine that the first detecting signal equals to the second detecting signal only if both the amount and the intensity of the first detecting signal are or approximately are the same as those of the second detecting signal. The term "approximately" may indicate ±20% variation of the value it describes, unless otherwise stated. As another example, if the processing device 140 determines either the amount or the intensity of the first detecting signal is or is approximately the same as that of the second detecting signal, the processing device 140 may determine that the first detecting signal equals to the second detecting signal.

If the processing device 140 determines that the first detecting signal does not equal to the second detecting signal, the process 1000 may proceed to 1040. In 1040, the processing device 140 may determine that a successful connection is not established between the scan platform 114 and the medical imaging device 110.

In 1050, the processing device 140 (e.g., the processing module 420, the control module 430) may return to connect the scan platform 114 to the medical imaging device 110. The connection method may be found elsewhere in the present disclosure (e.g., FIG. 9 and the description thereof). After operation 1050, the process 1000 may resume operations 1010 to 1030 to determine whether the first detecting signal equals the second detecting signal.

If the first detecting signal equals the second detecting signal, the process 1000 may proceed to operation 1060 to determine a successful connection established between the scan platform 114 and the medical imaging device 110. In some embodiments, the processing device 140 may output an indication indicative of the successful connection to, for example, a user.

It should be noted that the above description of the process 1000 is merely provided for illustration, and not intended to limit the scope of the present disclosure. For persons having ordinary skills in the art, multiple variations and modifications may be made to the process 1000 under the teachings of the present disclosure. However, those variations and modifications do not depart from the scope of the present disclosure. For example, the first detecting signal may be transmitted by the first optical fiber interface on the medical imaging device 110 and the second detecting signal may be acquired by the second optical fiber interface on the scan platform 114. As another example, there may be more than two optical fiber interfaces in the medical imaging system 100 to perform medical image scanning positioning in the process 1000.

Figure 11:
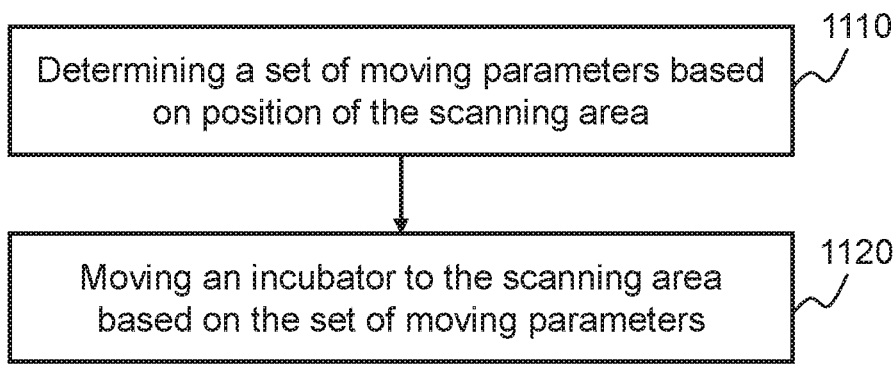
FIG. 11 is a flowchart illustrating an exemplary process for moving an incubator to a scanning area of a medical imaging device according to some embodiments of the present disclosure.

FIG. 11 is a flowchart illustrating an exemplary process for moving an incubator to a scanning area according to some embodiments of the present disclosure. In some embodiments, one or more operations of the process 1100 illustrated in FIG. 11 for medical image scanning positioning may be implemented in the medical imaging system 100 illustrated in FIG. 1. For example, the process 1100 illustrated in FIG. 11 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3). In some embodiments, the operation 740 of the process may be performed according to the process 1100.

In 1110, the processing device 140 (e.g., the processing module 420) may determine a set of moving parameters based on the position of the scanning area. In some embodiments, after connecting the scan platform 114 to the medical imaging device 110, the processing device 140 may obtain the position of the scanning object on the scan platform 114. An incubator may be arranged on the scan platform 114, and the scanning object may be a baby in the incubator. The set of moving parameters may be determined by the processing device 140 based on the position information of the baby on the scan platform 114 and the position information of the baby relative to the scanning area. The position information of the baby on the scan platform 114 and the position information of baby relative to the scanning area may be obtained by a photo taken by a camera (not shown) arranged in the medical imaging device 110.

In 1120, the processing device 140 (e.g., the processing module 420, the control module 430, the moving unit 520 of the processing module 420) may control the incubator to move to the scanning area based on the set of the moving parameters. After the set of moving parameters is determined by the processing device 140, the incubator may be controlled to move to the scanning area to conduct a medical imaging diagnoses.

It should be noted that the above description of the process 1100 is merely provided for illustration, and not intended to limit the scope of the present disclosure. For persons having ordinary skills in the art, multiple variations and modifications may be made to the process 1100 under the teachings of the present disclosure. However, those variations and modifications do not depart from the scope of the present disclosure. For example, a position of the scanning object may be obtained in 1110.

Figure 12:
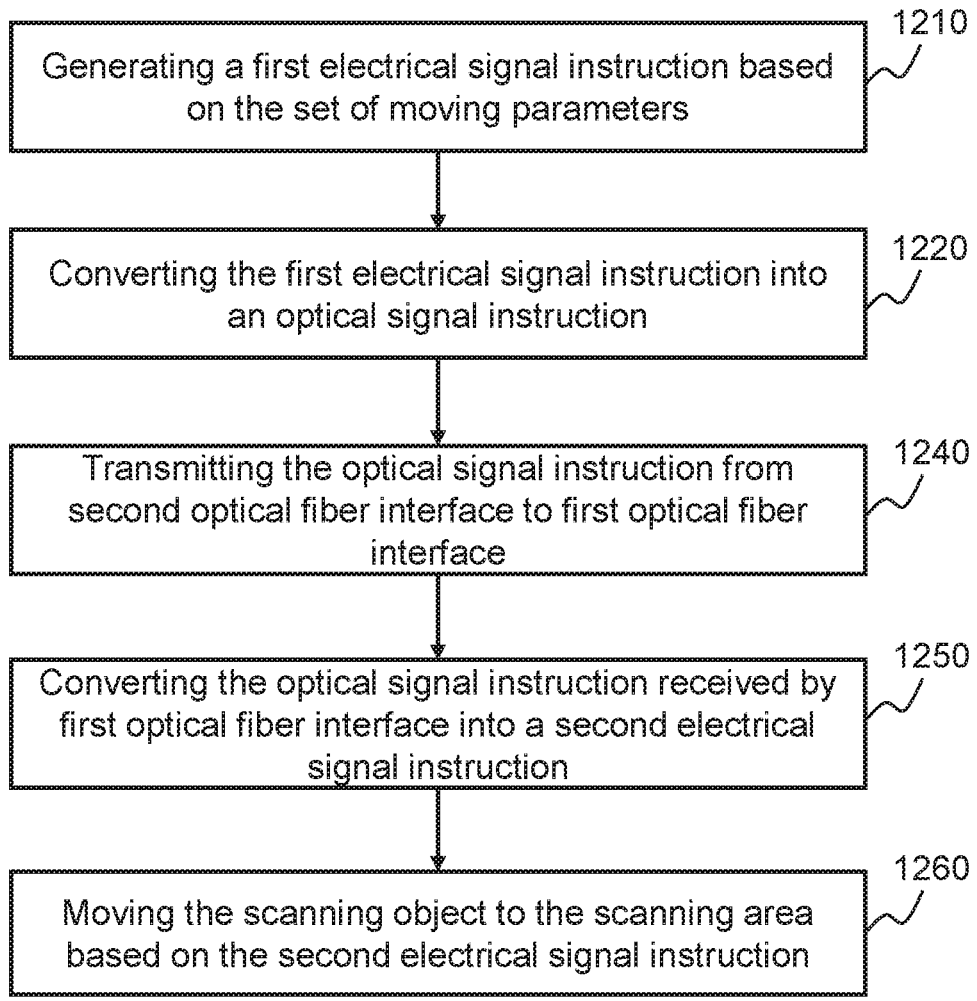
FIG. 12 is a flowchart illustrating an exemplary process for moving a scanning object to a scanning area of a medical imaging device according to some embodiments of the present disclosure.

FIG. 12 is a flowchart illustrating an exemplary process for moving a scanning object to a scanning area of a medical imaging device 110 according to some embodiments of the present disclosure. In some embodiments, one or more operations of the process 1200 illustrated in FIG. 12 for medical image scanning positioning may be implemented in the medical imaging system 100 illustrated in FIG. 1. For example, the process 1200 illustrated in FIG. 12 may be stored in the storage device 150 in the form of instructions, and invoked and/or executed by the processing device 140 (e.g., the processor 210 of the computing device 200 illustrated in FIG. 2, the CPU 340 of the mobile device 300 illustrated in FIG. 3). In some embodiments, the operation 740 of the process may be performed according to the process 1200.

In 1210, the processing device 140 (e.g., the processing module 420) may generate a first electrical signal instruction based on the set of moving parameters. The set of moving parameters may be movement data of the scan platform 114 to move the scanning object to the scanning area of the medical imaging device 110 as described elsewhere in the present disclosure. The movement data may include a movement distance, a movement direction, a movement speed, a movement route, or the like, or any combination thereof. The first electrical signal instruction may be a moving instruction associated with the set of moving parameters for the scan platform 114.

In 1220, the processing device 140 (e.g., the processing module 420) may convert the first electrical signal instruction into an optical signal instruction. In some embodiments, the first signal instruction may be converted into the optical signal instruction based on an optical transmitter installed on the medical imaging device 110. The optical transmitter may include a signal processor and an optical modulator. The signal processor may include a digital signal processor (DSP) and an analog signal processor (ASP). The optical modulator may include an internal modulation type and an external modulation type. The internal modulation type may convert the first electrical signal instruction into the optical signal instruction directly. The external modulation type may be associated with modulators including, for example, an electro-optic modulator (EOM), a magneto-optic modulator (MOM), an acousto-optic modulator (AOM), or the like, or any combination thereof. After the modulation, the optical signal instruction may be loaded on optical waves having certain vibration amplitude, frequency, phase, polarization state, duration, or the like, or any combination thereof.

In 1240, the processing device 140 (e.g., the processing module 420, the control module 430) may cause, for example, an optical fiber cable, to transmit the optical signal instruction from the second optical fiber interface to the first optical fiber interface.

In 1260, the processing device 140 (e.g., the processing module 420) may convert the optical signal instruction received by the first optical fiber interface into a second electrical signal instruction. The second electrical signal instruction may be same with the first electrical signal instruction including, for example, a movement distance, a movement direction, a movement speed, a movement route, or the like, or any combination thereof. In some embodiments, the optical signal instruction may be converted into the second electrical signal instruction based on an optical receiver installed on the scan platform 114. The optical receiver may include a photodetector, an amplifier, an automatic gain control (AGC) circuit, an optical demodulator, or the like, or any combination thereof. The photodetector may include a p-i-n photodiode (pin-PD), an avalanche photodiode (APD), etc. To convert the optical signal instruction into the second electrical signal effectively, the optical receiver may meet the requirements including, for example, high sensibility, low bit error rate, high signal to noise ratio, or the like, or any combination thereof.

In 1250, the processing device 140 (e.g., the processing module 420, the control module 430) may cause the movement part 620 of the scan platform 114 to move the scanning object to the scanning area based on the second electrical signal instruction.

Through operations 1210 to 1250, the electrical signal instruction based on the set of moving parameters may be transmitted between the medical imaging device 110 and the scan platform 114 through an optical signal. The optical signal, compared with the electrical signal, may have less effect on the medical imaging device and other components in the medical imaging system 100. The first optical interface and the second optical interface may also simplify the mechanical structure of the medical imaging device 110.

It should be noted that the above description of the process 1200 is merely provided for illustration, and not intended to limit the scope of the present disclosure. For persons having ordinary skills in the art, multiple variations and modifications may be made to the process 1200 under the teachings of the present disclosure. However, those variations and modifications do not depart from the scope of the present disclosure. For example, in 1210, the first electrical signal instruction may be pre-processed (e.g., filtered, de-noised, classified, or sorted) by the processing device 140. As another example, in 1240, the second electrical signal instruction may be post-processed by the processing device 140.

Figure 13A:
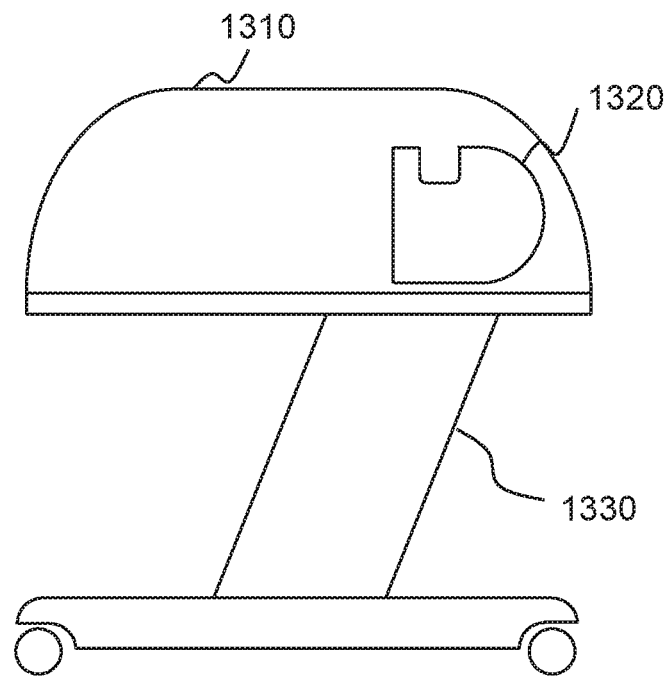
FIG. 13a is a schematic diagram illustrating a structure of an exemplary scan platform according to some embodiments of the present disclosure.

FIG. 13*a* is a schematic diagram illustrating a structure of an exemplary scan platform according to some embodiments of the present disclosure. In FIG. 13*a*, the scan platform 114 may be a pediatric scan platform. Reference number 1310 refers to an incubator, reference number 1320 refers to a helmet, and reference number 1330 refers to a bed body.

The incubator 1310 may locate on the bed body 1330 and connect to the bed body 1330 through a slide rail. The incubator 1310 may be configured to move in the horizontal direction relative to the bed body 1330. The incubator 1310 may be configured to carry a baby. The size of the incubator 1310 may be changed according to the size of the baby.

The helmet 1320 may be configured to protect the baby in the incubator 1310. Also, the helmet 1320 may be configured to determine the position of the baby in the incubator 1310. In some embodiments, the helmet 1320 may be configured to install a head coil for an MRI scanning. The size of the helmet 1320 may be changed according to the baby.

The bed body 1330 may be configured to support the incubator 1310. A plurality of wheels may be arranged in the bottom of the bed body 1330 enabling the scan platform 114 to move in the scanning room. The height of the scan platform 114 may be adjusted by adjusting the bed body 1320.

It should be noted that the above description of the structure of the scan platform is merely provided for illustration, and not intended to limit the scope of the present disclosure. For persons having ordinary skills in the art, multiple variations and modifications may be made to the structure of the scan platform under the teachings of the present disclosure. However, those variations and modifications do not depart from the scope of the present disclosure. The size of the scan platform 114, including the length, the height, and the weight, may be matched with the medical imaging device 110. The size of the scan platform 114 may be adjusted according to the demand information of the medical imaging device 110. A plurality of functional components (e.g., the wireless signal transmitter, the optical fiber interface, and the driving device) are not shown in the FIG. 13*a*.

Figure 13B:
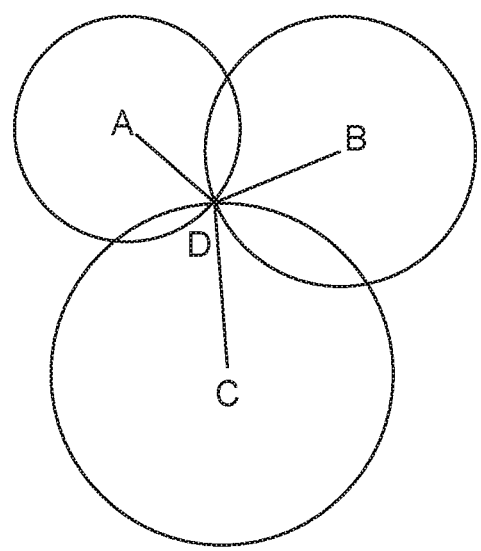
FIG. 13b is a schematic diagram illustrating exemplary ZigBee positioning technology according to some embodiments of the present disclosure.

FIG. 13*b* is a schematic diagram illustrating exemplary ZigBee positioning technology according to some embodiments of the present disclosure.

In FIG. 13*b*, there are three wireless signal transmitters A, B, and C respectively, and a scan platform 114 (marked as D). The coordinates of the three wireless signal transmitters are $(x_a, y_a)$, $(x_b, y_b)$, and $(x_c, y_c)$, respectively. The distances between the three wireless signal transmitters and the scan platform 114 may be designated as $d_a$, $d_b$, and $d_c$, respectively. In some embodiments, the scan platform 114 may include a wireless signal receiver, and $d_a$, $d_b$, and $d_c$ may be determined by the distances between the three wireless signal transmitters and the wireless signal receiver. If the coordinates of the scan platform 114 are (x, y), according to the formula of the distance between two points, $d_a$, $d_b$, and $d_c$ may be determined as:

$$\sqrt{(x-x_a)^2+(y-y_a)^2}=d_a,$$

$$\sqrt{(x-x_b)^2+(y-y_b)^2}=d_b,$$

$$(x-x_c)^2+(y-y_c)^2=d_c. \qquad (1)$$

According to the formula (1), the coordinates of the scan platform 114 may be determined as:

$$\begin{bmatrix} x \\ y \end{bmatrix} = \begin{bmatrix} 2(x_a - x_c) & 2(y_a - y_c) \\ 2(x_b - x_c) & 2(y_b - y_c) \end{bmatrix}^{-1} \begin{bmatrix} x_a^2 - x_c^2 + y_a^2 - y_c^2 + d_c^2 - d_a^2 \\ x_b^2 - x_c^2 + y_b^2 - y_c^2 + d_c^2 - d_b^2 \end{bmatrix}, \qquad (2)$$

where the distance between the wireless signal transmitters and the scan platform 114 may be determined by RSSI (Received Signal Strength Indication) ranging method, the relationship between the wireless signal transmitting power and wireless signal receiving power may be represented as: $P_R = P_T/r^n$, where $P_R$ is the receiving power of the wireless signal by a wireless signal receiver, $P_T$ is the transmitting power of the wireless signal, r is the distance between the wireless signal transmitter and the wireless signal receiver (e.g., $d_a$, $d_b$, or $d_c$), and n is the propagation factor, the value of which may be determined by the environment of the wireless transmission. In a given environment, n may be a fixed value. $d_a$, $d_b$, and $d_c$ may be determined according to the RSSI ranging method. The position information (e.g., the coordinates (x, y)) of the scan platform 114 in the scanning room may be determined according to the formula (1) and/or the formula (2).

It should be noted that the above description of the ZigBee positioning technology is merely provided for illustration, and not intended to limit the scope of the present disclosure. For persons having ordinary skills in the art, multiple variations and modifications may be made to the ZigBee positioning technology under the teachings of the present disclosure. However, those variations and modifications do not depart from the scope of the present disclosure.

Figure 14:
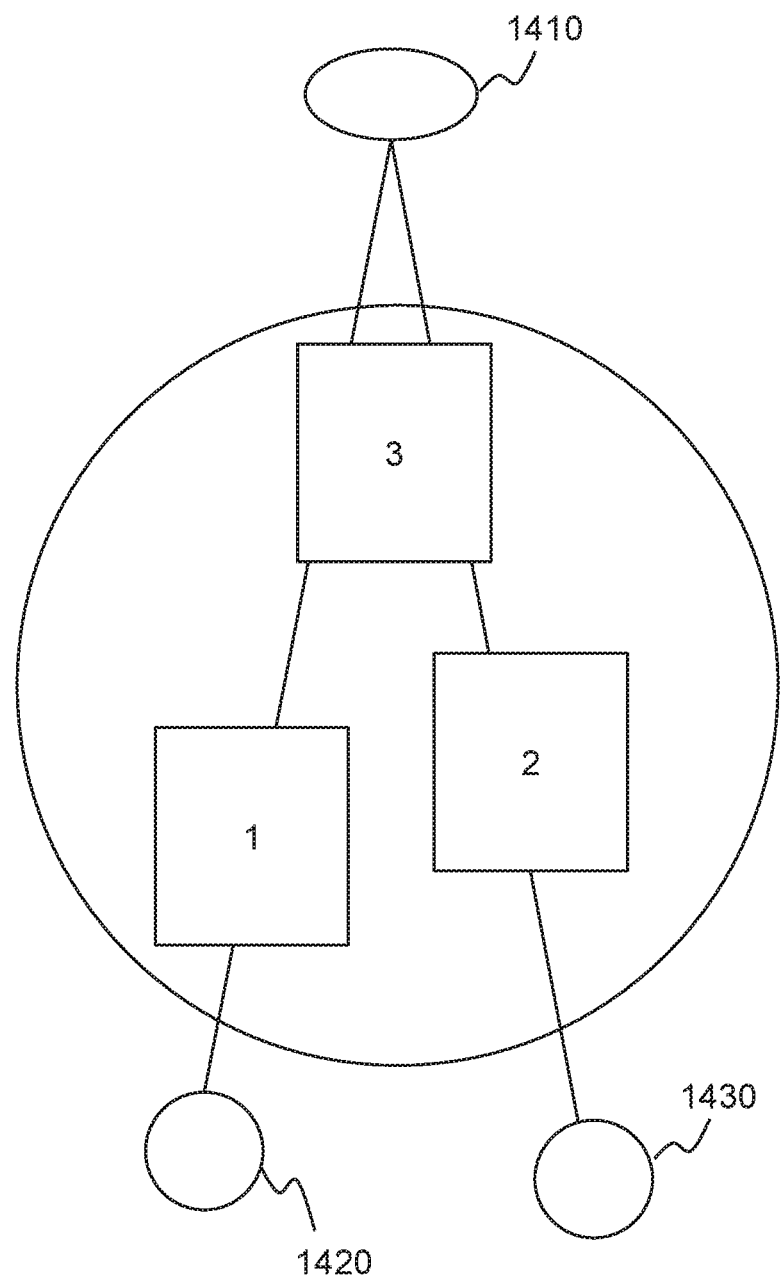
FIG. 14 is a schematic diagram illustrating an exemplary process for moving a scan platform to an appropriate position for connecting to the medical imaging device according to some embodiments of the present disclosure.

FIG. 14 is a schematic diagram illustrating an exemplary process of moving a scan platform 114 to an appropriate position for connecting to the medical imaging device 110 according to some embodiments of the present disclosure. In FIG. 14, reference number 1410 refers to an optical signal transmitter, reference numbers 1420 and 1430 respectively refer to two optical signal receivers, and reference number 1440 refers to the joint area. Reference numbers 1, 2, and 3 refer to three sub-areas in the joint area.

The optical signal transmitter 1410 may transmit optical signals, and the two optical signal receivers 1420 and 1430 may receive the optical signals transmitted by the optical signal transmitter 1410. In some embodiments, the optical signal transmitter 1410 may be arranged under the optical fiber interface of the medical imaging device 110. The two optical signal receivers 1420-1430 may be arranged on the wall of the scanning room. In some embodiments, the positions of the optical signal transmitter 1410 and the two optical signal receivers 1420-1430 may also be set according to the detailed position information of the medical imaging device 110 in the scanning room.

In some embodiments, a transparent region may be arranged on the scan platform 114. The transparent region may be a region for the optical signals to pass through. The height of the center of the transparent region may equal to the optical signal transmitters and the optical signal receivers. Two shading components (e.g., two shading boards, two shading blocks) may be arranged in the transparent region. Each of the two shading components may include a visor for blocking the optical signals. After the scan platform 114 moves to the joint area 1440, the optical signal transmitter 1410 may be actuated to emit optical signals. The optical signals may pass through the transparent region and received by the two optical signal receivers 1420 and 1430.

The processing device 140 (e.g., the processing module 420) may determine a position adjusting information based on the intensities of optical signals transmitted by the optical signal transmitter 1410 and the intensities of optical signals received by the two optical signal receivers 1420 and 1430. The position adjusting information may be an adjustment to the moving path. For example, when the scan platform 114 moves to the subarea 1, the intensities of the optical signals received by the optical signal receiver 1420 may be larger than zero. The processing device 140 may determine the position adjusting information to be the adjustment to the moving path of the scan platform 114 to move to the right. When the scan platform 114 moves to the subarea 2, the intensities of the optical signals received by the optical signal receiver 1430 may be larger than zero. The processing device 140 may determine the position adjusting information to be the adjustment to the moving path of the scan platform 114 to move to the left. In some embodiments, the processing device 140 may determine an adjusting time threshold. If the number of actual adjustments is larger than the adjusting time threshold, the position adjusting information may be determined to be the adjustment to the moving path of the scan platform 114 to move toward the optical signal transmitter 1410. When the scan platform moves to the subarea 3, the intensities of the optical signals received by the optical signal receivers 1420 and 1430 may both equal to zero. The processing device 140 may determine the scan platform 114 in the subarea as an appropriate location.

In some embodiments, a shading region may be arranged on the scan platform 114, and two transparent subregions are arranged in the shading region. The processing device 140 may determine an appropriate position for the scan platform 114 in the joint area based on the two transparent subregions. The processing device 140 may control the scan platform 114 to move to the appropriate position and connect the scan platform 114 to the medical imaging device 110.

It should be noted that the above description of the process of moving the scan platform 114 to an appropriate position for connecting to the medical imaging device 110 is merely provided for illustration, and not intended to limit the scope of the present disclosure. For persons having ordinary skills in the art, multiple variations and modifications may be made to the process of moving the scan platform to the appropriate position under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
a storage device storing a set of instructions; and
one or more processors configured to communicate with the storage device, wherein when executing the set of instructions, the one or more processors are configured to cause the system to:
detect, by a signal detecting device, an entrance of a scan platform into a scanning room, wherein
the scan platform is configured to support a scanning object,
a transparent region is arranged on the scan platform, and
two shading components are arranged in the transparent region;
move the scan platform to a joint area according to a connection interface of a medical imaging device;
actuate an optical signal transmitter to emit optical signals toward two optical signal receivers, the optical signal transmitter being on one side of the joint area, the two optical signal receivers being configured to receive the optical signals emitted by the optical signal transmitter;
determine an intensity of optical signals received by the two optical signal receivers;
determine whether the intensity of the optical signals received by the two optical signal receivers equals zero, wherein
each of the two shading components in the transparent region is configured to block the optical signals emitted by the optical signal transmitter so that the intensity of the optical signals received by at least one of the two optical signal receivers is zero, and
the transparent region of the scan platform, except for the two shading components, is configured to allow passage of the optical signals emitted by the optical signal transmitter so that the intensity of the optical signals received by the two optical signal receivers is non-zero;
determine, in response to the determination that the intensity of the optical signals received by at least one of the two optical signal receivers does not equal zero, the scan platform is not at a position suitable to connect to the medical imaging device;
determine, based on the intensity of the optical signals received by the two optical signal receivers, position adjusting information of the scan platform; and
adjust, based on the position adjusting information, a moving path of the scan platform until the scan platform is moved to the position suitable to connect to the medical imaging device;
determine, in response to the determination that the intensity of the optical signals received by the two optical signal receivers equals zero, the scan platform is at the position suitable to connect to the medical imaging device;
connect, by a physical interface and within the joint area, the scan platform to the medical imaging device; and
move the scanning object to a scanning area of the medical imaging device.

2. The system of claim 1, wherein to adjust the scan platform,
the scan platform includes a first optical fiber interface;
the medical imaging device includes a second optical fiber interface; and
the one or more processors are further configured to cause the system to:
before actuating the optical signal transmitter to emit optical signals, adjust the scan platform such that a height of the first optical fiber interface is consistent with a height of the second optical fiber interface.

3. The system of claim 2, wherein the first optical fiber interface and the second optical interface are arranged in two opposite sides of the joint area.

4. The system of claim 1, wherein the one or more processors are further configured to cause the system to:
transmit, by a first optical fiber interface, a first detecting signal;
receive, by a second optical fiber interface, a second detecting signal;
determine whether the first detecting signal equals the second detecting signal;
determine, in response to the determination that the first detecting signal equals the second detecting signal, that a successful connection is established between the scan platform and the medical imaging device; and
output an indication indicative of the successful connection.

5. The system of claim 4, wherein the one or more processors are further configured to cause the system to:
determine, in response to the determination that the first detecting signal does not equal the second detecting signal, that a successful connection is not established between the scan platform and the medical imaging device; and attempt again to connect the scan platform to the medical imaging device.

6. The system of claim 1, wherein to move the scanning object to a scanning area of the medical imaging device, the one or more processors are configured to cause the system to:
 determine a set of moving parameters based on a location of the scanning area, an initial position of the scanning object in the scan platform, and a position of scan platform after connecting with the medical imaging device; and
 move, based on the set of moving parameters, the scanning object to the scanning area.

7. The system of claim 6, wherein the one or more processors are further configured to cause the system to:
 generate, based on the set of moving parameters, a first electrical signal instruction;
 convert the first electrical signal instruction into an optical signal instruction;
 transmit the optical signal instruction from a second optical fiber interface to a first optical fiber interface;
 convert the optical signal instruction received by the first optical fiber interface into a second electrical signal instruction; and
 move, based on the second electrical signal instruction, the scanning object to the scanning area.

8. The system of claim 1, wherein the scan platform is a pediatric scan platform including a bed body and an incubator.

9. The system of claim 1, wherein to move the scan platform to the joint area, the one or more processors are configured to cause the system to:
 obtain a position of the scan platform and a position of the joint area;
 determine, based on the position of the scan platform and the position of the joint area, a route; and
 move the scan platform to the joint area according to the route.

10. The system of claim 9, wherein to determine the route, the one or more processors are further configured to cause the system to:
 obtain position information of the scan platform based on a wireless positioning technology, internal image information of the scanning room using at least one camera arranged in the scanning room, and position information of the joint area determined based on the optical signal transmitter and the two optical signal receivers, the position information of the scan platform comprising a position of the scan platform when the scan platform enters the scanning room;
 determine whether an obstacle exists in the scanning room based on the internal image information;
 in response to determining that the obstacle exists in the scanning room, determine, based on the position information of the scan platform, the internal image information of the scanning room, the position information of the joint area, and the existence of the obstacle, a route from the position of the scan platform when the scan platform enters the scanning room to the joint area.

11. The system of claim 10, wherein to determine, based on the position information of the scan platform, the internal image information, and the position information of the joint area, a route, the one or more processors are configured to cause the system to:
 determine whether a historical route corresponding to the position information of the scan platform, the internal image information, and the position information of the joint area exists; and
 in response to determining that the historical route exists, designate the historical route as the route.

12. The system of claim 10, wherein to determine the route, the one or more processors are further configured to cause the system to:
 obtain internal image information of the scanning room using at least one camera arranged in the scanning room;
 determine whether an obstacle exists in the scanning room;
 construct a two-dimension map model or a three-dimension map model of the scanning room based on the internal image information and the obstacle if it exists; and
 in response to determining that the obstacle exists in the scanning room, determine, based on the two-dimension map model or the three-dimension map model, the position information of the scan platform, the position information of the joint area, and the existence of the obstacle, the route from the position of the scan platform when the scan platform enters the scanning room to the joint area.

13. A method for connecting a scan platform to a medical imaging device, the method being implemented on at least one machine each of which has one or more processors and a storage device, comprising:
 detecting, by a signal detecting device, an entrance of the scan platform into a scanning room, wherein
  the scan platform is configured to support a scanning object,
  a transparent region is arranged on the scan platform, and
  two shading components are arranged in the transparent region;
 moving the scan platform to a joint area according to a connection interface of the medical imaging device;
 actuating an optical signal transmitter to emit optical signals toward two optical signal receivers, the optical signal transmitter being on one side of the joint area, the two optical signal receivers being configured to receive the optical signals emitted by the optical signal transmitter;
 determining an intensity of optical signals received by the two optical signal receivers;
 determining whether the intensity of the optical signals received by the two optical signal receivers equals zero, wherein
  each of the two shading components in the transparent region is configured to block the optical signals emitted by the optical signal transmitter so that the intensity of the optical signals received by at least one of the two optical signal receivers is zero, and
  the transparent region of the scan platform, except for the two shading components, is configured to allow passage of the optical signals emitted by the optical signal transmitter so that the intensity of the optical signals received by the two optical signal receivers is non-zero;
 determining, in response to the determination that the intensity of the optical signals received by at least one of the two optical signal receivers does not equal zero, the scan platform is not at a position suitable to connect to the medical imaging device;

determining, based on the intensity of the optical signals received by the two optical signal receivers, position adjusting information of the scan platform; and adjusting, based on the position adjusting information, a moving path of the scan platform until the scan platform is moved to the position suitable to connect to the medical imaging device;

determining, in response to the determination that the intensity of the optical signals received by the two optical signal receivers equals zero, the scan platform is at the position suitable to connect to the medical imaging device;

connecting, by a physical interface and within the joint area, the scan platform to the medical imaging device; and moving the scanning object to a scanning area of the medical imaging device.

14. The method of claim 13, wherein the adjusting the scan platform comprising:

the scan platform includes a first optical fiber interface;
the medical imaging device includes a second optical fiber interface; and
the method further includes:
before actuating the optical signal transmitter to emit optical signals, adjusting the scan platform such that a height of the first optical fiber interface is consistent with a height of the second optical fiber interface.

15. The method of claim 13, further comprising:

transmitting, by a first optical fiber interface, a first detecting signal;
receiving, by a second optical fiber interface, a second detecting signal;
determining whether the first detecting signal equals the second detecting signal;
determining, in response to the determination that the first detecting signal equals the second detecting signal, that a successful connection is established between the scan platform and the medical imaging device; and
outputting an indication indicative of the successful connection.

16. The method of claim 15, further comprising:

determining, in response to the determination that the first detecting signal does not equal the second detecting signal, that a successful connection is not established between the scan platform and the medical imaging device; and
attempting again to connect the scan platform to the medical imaging device.

17. The method of claim 13, wherein moving the scanning object to a scanning area of the medical imaging device comprises:

determining a set of moving parameters based on a location of the scanning area, an initial position of the scanning object in the scan platform, and a position of scan platform after connecting with the medical imaging device; and
moving, based on the set of moving parameters, the scanning object to the scanning area.

18. The method of claim 17, further comprising:

generating, based on the set of moving parameters, a first electrical signal instruction;
converting the first electrical signal instruction into an optical signal instruction;
transmitting the optical signal instruction from a second optical fiber interface to a first optical fiber interface;
converting the optical signal instruction received by the first optical fiber interface into a second electrical signal instruction; and
moving, based on the second electrical signal instruction, the scanning object to the scanning area.

19. A non-transitory computer readable medium comprising executable instructions that, when executed by a computing device, cause the computing device to effectuate a method, the method comprising:

detecting, by a signal detecting device, an entrance of a scan platform into a scanning room, wherein
the scan platform is configured to support a scanning object,
a transparent region is arranged on the scan platform, and
two shading components are arranged in the transparent region;
moving the scan platform to a joint area according to a connection interface of a medical imaging device;
actuating an optical signal transmitter to emit optical signals toward two optical signal receivers, the optical signal transmitter being on one side of the joint area, the two optical signal receivers being configured to receive the optical signals emitted by the optical signal transmitter;
determining an intensity of optical signals received by the two optical signal receivers;
determining whether the intensity of the optical signals received by the two optical signal receivers equals zero, wherein
each of the two shading components in the transparent region is configured to block the optical signals emitted by the optical signal transmitter so that the intensity of the optical signals received by at least one of the two optical signal receivers is zero, and
the transparent region of the scan platform, except for the two shading components, is configured to allow passage of the optical signals emitted by the optical signal transmitter so that the intensity of the optical signals received by the two optical signal receivers is non-zero;
determining, in response to the determination that the intensity of the optical signals received by at least one of the two optical signal receivers does not equal zero, the scan platform is not at a position suitable to connect to the medical imaging device;
determining, based on the intensity of the optical signals received by the two optical signal receivers, position adjusting information of the scan platform; and
adjusting, based on the position adjusting information, a moving path of the scan platform until the scan platform is moved to the position suitable to connect to the medical imaging device;
determining, in response to the determination that the intensity of the optical signals received by the two optical signal receivers equals zero, the scan platform is at the position suitable to connect to the medical imaging device;
connecting, by a physical interface and within the joint area, the scan platform to the medical imaging device; and
moving the scanning object to a scanning area of the medical imaging device.

* * * * *